US009430615B2

United States Patent
Michaelis et al.

(10) Patent No.: US 9,430,615 B2
(45) Date of Patent: Aug. 30, 2016

(54) PERSONAL ELECTRONIC DEVICES WITH UNOBTRUSIVE EKG-BASED DETECTION OF HEART RATE AND RHYTHM ANOMALIES

(71) Applicant: Avaya Inc., Basking Ridge, NJ (US)

(72) Inventors: Paul Roller Michaelis, Louisville, CO (US); Jon Bentley, New Providence, NJ (US)

(73) Assignee: Avaya Inc., Basking Ridge, NJ (US)

( * ) Notice: Subject to any disclaimer, the term of this patent is extended or adjusted under 35 U.S.C. 154(b) by 0 days.

(21) Appl. No.: 13/930,388

(22) Filed: Jun. 28, 2013

(65) Prior Publication Data

US 2015/0005653 A1    Jan. 1, 2015

(51) Int. Cl.
| | |
|---|---|
| *A61B 5/0402* | (2006.01) |
| *G06F 19/00* | (2011.01) |
| *A61B 5/024* | (2006.01) |
| *A61B 5/0245* | (2006.01) |
| *A61B 5/00* | (2006.01) |
| *A61B 5/0408* | (2006.01) |

(52) U.S. Cl.
CPC ....... *G06F 19/3418* (2013.01); *A61B 5/02438* (2013.01); *A61B 5/02455* (2013.01); *A61B 5/0022* (2013.01); *A61B 5/0408* (2013.01); *A61B 5/6803* (2013.01); *A61B 5/6815* (2013.01); *A61B 5/6898* (2013.01); *A61B 5/746* (2013.01); *A61B 2505/07* (2013.01); *G06F 19/345* (2013.01)

(58) Field of Classification Search
CPC  A61B 5/0006; A61B 5/0402; A61B 5/0404; A61B 5/0485; A61B 5/6802; A61B 5/6803; A61B 5/681; A61B 5/6898; G06F 19/3418
USPC ...................................... 600/508–518; 705/2
See application file for complete search history.

(56) References Cited

U.S. PATENT DOCUMENTS

| | | | |
|---|---|---|---|
| 7,925,508 B1 | 4/2011 | Michaelis | |
| 8,700,137 B2 * | 4/2014 | Albert | 600/513 |
| 2011/0301435 A1 * | 12/2011 | Albert et al. | 600/301 |
| 2013/0005303 A1 * | 1/2013 | Song et al. | 455/411 |

OTHER PUBLICATIONS

U.S. Appl. No. 13/905,942, filed May 20, 2013, Michaelis et al.
U.S. Appl. No. 13/832,741, filed Mar. 15, 2013, Bentley et al.
U.S. Appl. No. 13/867,769I, filed Apr. 22, 2013, Bentley et al.
U.S. Appl. No. 13/846,243, filed Mar. 18, 2013, Bentley et al.

(Continued)

*Primary Examiner* — Allen Porter, Jr.
(74) *Attorney, Agent, or Firm* — Sheridan Ross P.C.

(57) ABSTRACT

A personal electronic device is configured to unobtrusively detect heart rate and rhythm anomalies utilizing an electrocardiogram (EKG)-based detection and monitoring method. As one example, while a user is using the personal electronic device for its intended function, such as communicating, playing music, and/or watching videos, the personal electronic device may be unobtrusively detecting and recording a user's heart rate and heart rhythm to detect anomalies. For instance, while a user is making a phone call, electrodes of the personal electronic device located in the vicinity of the earpiece and on the handset, may come into contact with a user's ear and a user's hand respectively. Thus, while the personal electronic device is being consciously used for a function other than EKG monitoring, EKG monitoring is unobtrusively occurring.

21 Claims, 8 Drawing Sheets

(56) References Cited

OTHER PUBLICATIONS

Barill, "Chapter 4: ECG Primer," in "The Six Second ECG," Nursecom Educational Technologies, pp. 63-100, Apr. 2005.

Casillas, "Heart Rate Monitor and Electrocardiograph Fundamentals," Mar. 2010, Freescale Semiconductor, available at www.freescale.com/files/microcontrollers/doc/app_note/AN4059.pdf, 22 pages.

Chi et al., "Wireless Non-contact EEG/ECG Electrodes for Body Sensor Networks," Proc. Body Sensor Networks (BSN 2010), Jun. 7-9, 2010 available at www.isn.ucsd.edu/pubs/bsn10.pdf, 5 pages.

Da He et al., "The ear as a location for wearable vital signs monitoring." IEEE, 32nd Annual International Conference of the IEEE EMBS, Aug. 31-Sep. 4, 2010, pp. 6389-6392 available at www.hdl.handle.net/1721.1/69025.

De Armas, "Design of a Non-intrusive 2-lead ECG System Using the Active Insulated Electrode," EE 4B16 Electrical Engineering Biomedical Capstones, Paper 24, 2010, available at www.digitalcommons.mcmaster.ca/ee4bi6/24, 45 pages.

Iozzio, "Electrocardiogram-Equipped Cell Phone Allows Remote Monitoring," Oct. 25, 2013, available at www.popsci.com/gadgets/article/2010-10/electrocardiogram-equipped-cell-phone-allows-remote-monitoring, 2 pages.

Jenkins, "Chapter I Basic Principles of ECG Interpretation," Nurse to Nurse, New York: McGraw-Hill Medical, 2010, available at www.mhprofessional.com/downloads/products/0071592830/01-jenkins_ch01_p01-026.pdf, 26 pages.

Jurik et al., "Mobile health monitoring through biotelemetry," Proceedings of the Fourth International Conference on Body Area Networks (BodyNets '09), ICST (Institute for Computer Sciences, Social-Informatics and Telecommunications Engineering), ICST, Brussels, Belgium, Belgium, Apr. 1-3, 2009, Article 12, DOI=10.4108/ICST.BODYNETS2009.5835, available at www.dx.doi.org/10.4108/ICST.BODYNETS2009.5835, 8 pages.

Karplus, "BME 194: Applied Circuits Lab 10: EKG," Mar. 7, 2013, available at www.users.soe.ucsc.edu/~karplus/bme194/w13/lab-handouts/10-EKG.pdf, 5 pages.

Lee et al., "Biopotential Electrode Sensors in ECG/EEG/EMG Systems," Analog Devices, Inc., 2008, available at www.analog.com/static/imported-files/tech_docs/ECG-EEG-EMG_FINAL.pdf, 2 pages.

Palca, "Cellphone Medical Test Wins NPR's 'Big Idea' Contest : NPR", Sep. 5, 2012, available at www.npr.org/2012/09/05/160542842/cellphone-medical-test-wins-nprs-big-idea-contest, 3 pages.

Raju, "Heart-Rate and EKG Monitor using the MSP430FG439", SLAA280, 2007, available at www.ti.com/lit/an/slaa280a/slaa280a.pdf, 12 pages.

Roach, "17-year-old girl invents heart exam for cellphones," Sep. 10, 2012, available at www.nbcnews.com/technology/futureoftech/17-year-old-girl-invents-heart-exam-cellphones-990117, 3 pages.

Townsend, "Medical Electronics", pp. 9-18, Term 2001, available at www.robots.ox.ac.uk/~neil/teaching/lectures/med_elec/notes2.pdf.

Tsu-Wang et al., "An ear-lead ECG based smart sensor system with voice biofeedback for daily activity monitoring," TENCON 2008—2008 IEEE Region 10 Conference, Nov. 19-21, 2008, 6 pages.

Van Mieghem, "The Clinical Value of the ECG in Noncardiac Conditions," Chest J., 2004, vol. 125(4), pp. 1561-1576 available at www.journal.publications.chestnet.org/data/Journals/CHEST/22007/1561.pdf.

Zhou et al., "A new system dedicated to real time cardiac arrhythmias tele-assistance and monitoring," J. Univers. Comput. Sci., 2006, vol. 12, pp. 30-44, available at www.jucs.org/jucs_12_1/a_new_system_dedicated/jucs_12_01_0030_0044_zhou.pdf.

"AliveCor Heart Monitor," AilveCor, retrieved from http://www.alivecor.com/?gclid=CMaZj7OA8LQCFegWMgodb1wAjA [retrieved Jul. 1, 2013], 6 pages.

\* cited by examiner

PERSONAL ELECTRONIC DEVICES WITH UNOBTRUSIVE EKG-BASED DETECTION OF HEART RATE AND RHYTHM ANOMALIES

FIELD OF THE DISCLOSURE

An exemplary embodiment is generally directed toward unobtrusively detecting heart rate and heart rhythm anomalies from personal electronic devices that are consciously being used for a function other than electrocardiographic monitoring, such as listening to music.

BACKGROUND

Heart rate and rhythm irregularities can sometimes have catastrophic consequences. A heart rate that is too fast is referred to as tachycardia, while a heart rate that is too slow is referred to as bradycardia. A rhythm disturbance or arrhythmia is a condition in which the chambers of the heart do not contract in the appropriate sequence or with the appropriate timing. For example, in a type of arrhythmia known as atrial fibrillation, the upper chambers of the heart tend to quiver or contract in a disorganized manner. The resulting turbulence tends to form blood clots, which can travel downstream to a location where they causes a blockage (e.g., a stroke).

Many types of heart rhythm irregularity, including atrial fibrillation, cause no pain or discomfort. Although the causes of such arrhythmias tend to be treatable, and the likelihood of inappropriate clotting thereby reduced significantly, it is necessary first to know that the condition exists. Because episodes of arrhythmia tend to be painless and transient, the need for treatment might not be identified by a health care professional unless the episode occurs, perhaps coincidentally, while the patient is being examined.

Portable heart rate monitors, capable of detecting rate and rhythm irregularities, are well known. Some rely on simple two-lead electrocardiographic analysis, a good example being the devices commonly found in health clubs that can show the user's heart rate when the user touches the electrodes on the two hand grips of, for instance, an exercise bicycle. Another common technique can detect rate and rhythm irregularities optically, via a process known as photoplethysmography, which is the method underlying pulse oximeters. However, these conventional portable heart monitors require the user to initiate the monitoring.

SUMMARY

Given the transient and painless nature of many rate and rhythm irregularities, and given also that people must take deliberate steps in order to be monitored, there is a need for a device that can detect rate and rhythm irregularities as a background function while the device is being used for unrelated common activities. It is with respect to the above issues and other problems that the embodiments presented herein were contemplated.

In accordance with embodiments of the present invention, personal electronic devices, such as telephones and media players, having the ability to monitor the electrocardiogram (EKG) of a user are provided. Generally, electrode locations for a two-lead EKG may be such that the shortest pathway through the body from one electrode to the other would pass through the heart. Using as an example the exercise bicycle heart rate monitor described above, the shortest pathway between the user's two hands passes through the user's upper chest and therefore approximately through the heart. With regard to embodiments of the proposed invention, it is important to note that electrodes do not have to be placed at locations where the shortest pathway through the body from one electrode to the other passes through the heart in order to detect the "QRS complex" component of an EKG signal (which has a highly distinctive shape and occurs with every heart beat). For example, even though electrodes may be placed at less-than-optimal locations, the QRS complex is detectable with one electrode on either hand, and the other electrode on either ear. Therefore, embodiments of the present invention may utilize this ear-and-limb (e.g. ear-and-arm) electrode arrangement to monitor heart rate and rhythm and to detect anomalies.

For example, in one embodiment consistent with the present disclosure, an electrode would be placed on the earpiece of a wired or wireless handset of a telephone, with the second electrode placed where the user's hand comes in contact with the handset. The shape of the handset and the electrode locations may be crafted to ensure that the user doesn't "short out" the EKG signal, for example by touching the side of his head with the hand that is holding the handset. (And even if a contorted user does short the signal, that short will be detected, and not falsely interpreted.)

In another embodiment consistent with the present disclosure, conductive ear buds or earphones may provide an alternative to the handset earpiece electrode. When used in this configuration, the handset may not need to be held in the hand, as such an arrangement would provide equally good results if the handset is held against the arm with an elastic band (a common location when people are engaged in physical activity). Note also that this configuration may be implemented in a wide range of devices in addition to phones, such as music players (e.g. iPod®) and hand-held video players. In some embodiments, users will not need to take steps to initiate the heart rate and rhythm monitoring. Instead, heart rate and rhythm monitoring will occur automatically in the background, or as a background process, whenever the device is being used for its primary intended purpose, such as telephone conversations, listening to music, and watching videos.

In some instances, the personal electronic device may detect a potentially dangerous cardiac rhythm. In such occurrences, the personal electronic device may perform one of many possible options; such options may include, but are not limited to immediately calling 9-1-1, notifying one or more health care providers of the detected situation, sending heart rate and rhythm information to one or more health care providers, providing a subtle warning to the user after many detected events, and providing a gentle suggestion to the user recommending they conduct a more thorough heart rate and rhythm test and/or tell their health care provider anomalous event or events may have been detected. In some embodiments, more elaborate schemes could adjust the response based on the medical history of the user and the history of critical events. For example, if the device is capable of Internet communication, the device may relay key parameters of an anomalous rhythm to the user's health care providers, thereby allowing the healthcare provider to assess the situation and provide an appropriate recommendation and/or response. Moreover, additional features may provide the ability to record and time-stamp all interesting events.

In one embodiment, a method is provided that comprises: operating a personal electric device in a manner consistent with a first use of the personal electric device; measuring, between two electrodes associated with the personal electronic device, a differential voltage corresponding to electrical activity of a heart, wherein the measuring is unobtrusive and the first use of the personal electric device is other than electrocardiographic (EKG) monitoring; based on a processed differential voltage corresponding to electrical activity of the heart, determining an anomaly associated with the electrical activity of the heart; and providing at least one of an audio notification, a visual notification, and a tactile feedback notification of the determined anomaly.

In yet a further embodiment, a personal electronic device that provides unobtrusive detection of heart rate and heart rhythm anomalies while operating in a manner consistent with a first of the personal electronic device, the system comprising: at least two electrodes associated with the personal electronic device, the at least two electrodes positioned such that a differential voltage corresponding to electrical activity of the heart is detected and measured; a cardiac data analyzer that processes and analyzes the detected and measured differential voltage corresponding to electrical activity of the heart to provide a determined anomaly associated with the electrical activity of the heart; and at least one of a display, a speaker, and a tactile feedback component that outputs a notification associated with the determined anomaly; wherein the detecting and measuring of the differential voltage corresponding to electrical activity of the heart is unobtrusive and a first use of the personal electric device is other than electrocardiographic (EKG) monitoring.

In yet a further embodiment, a non-transitory computer readable information storage medium having stored thereon instructions that cause a computing system to execute a method is provided, the method comprising operating a personal electric device in a manner consistent with a first use of the personal electric device; measuring, between two electrodes associated with the personal electronic device, a differential voltage corresponding to electrical activity of a heart, wherein the measuring is unobtrusive and the first use of the personal electric device is other than electrocardiographic (EKG) monitoring; based on a processed differential voltage corresponding to electrical activity of the heart, determining an anomaly associated with the electrical activity of the heart; and providing at least one of an audio notification, a visual notification, and a tactile feedback notification of the determined anomaly.

In general, the term electrocardiogram is abbreviated as EKG and/or ECG, as EKG and ECG mean the same thing. As used herein, electrocardiogram will be abbreviated as EKG.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any tangible storage that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, or any other medium from which a computer can read. When the computer-readable media is configured as a database, it is to be understood that the database may be any type of database, such as relational, hierarchical, object-oriented, and/or the like. Accordingly, the disclosure is considered to include a tangible storage medium and prior art-recognized equivalents and successor media, in which the software implementations of the present disclosure are stored.

The terms "determine", "calculate", and "compute," and variations thereof, as used herein, are used interchangeably and include any type of methodology, process, mathematical operation or technique.

The term "module" as used herein refers to any known or later developed hardware, software, firmware, artificial intelligence, fuzzy logic, or combination of hardware and software that is capable of performing the functionality associated with that element. Also, while the disclosure is described in terms of exemplary embodiments, it should be appreciated that individual aspects of the disclosure can be separately claimed.

BRIEF DESCRIPTION OF THE DRAWINGS

Exemplary embodiments of the present disclosure are described in conjunction with the appended figures where.

DETAILED DESCRIPTION

The ensuing description provides embodiments only, and is not intended to limit the scope, applicability, or configuration of the claims. Rather, the ensuing description will provide those skilled in the art with an enabling description for implementing the embodiments. It being understood that various changes may be made in the function and arrangement of elements without departing from the spirit and scope of the appended claims.

Figure 1:
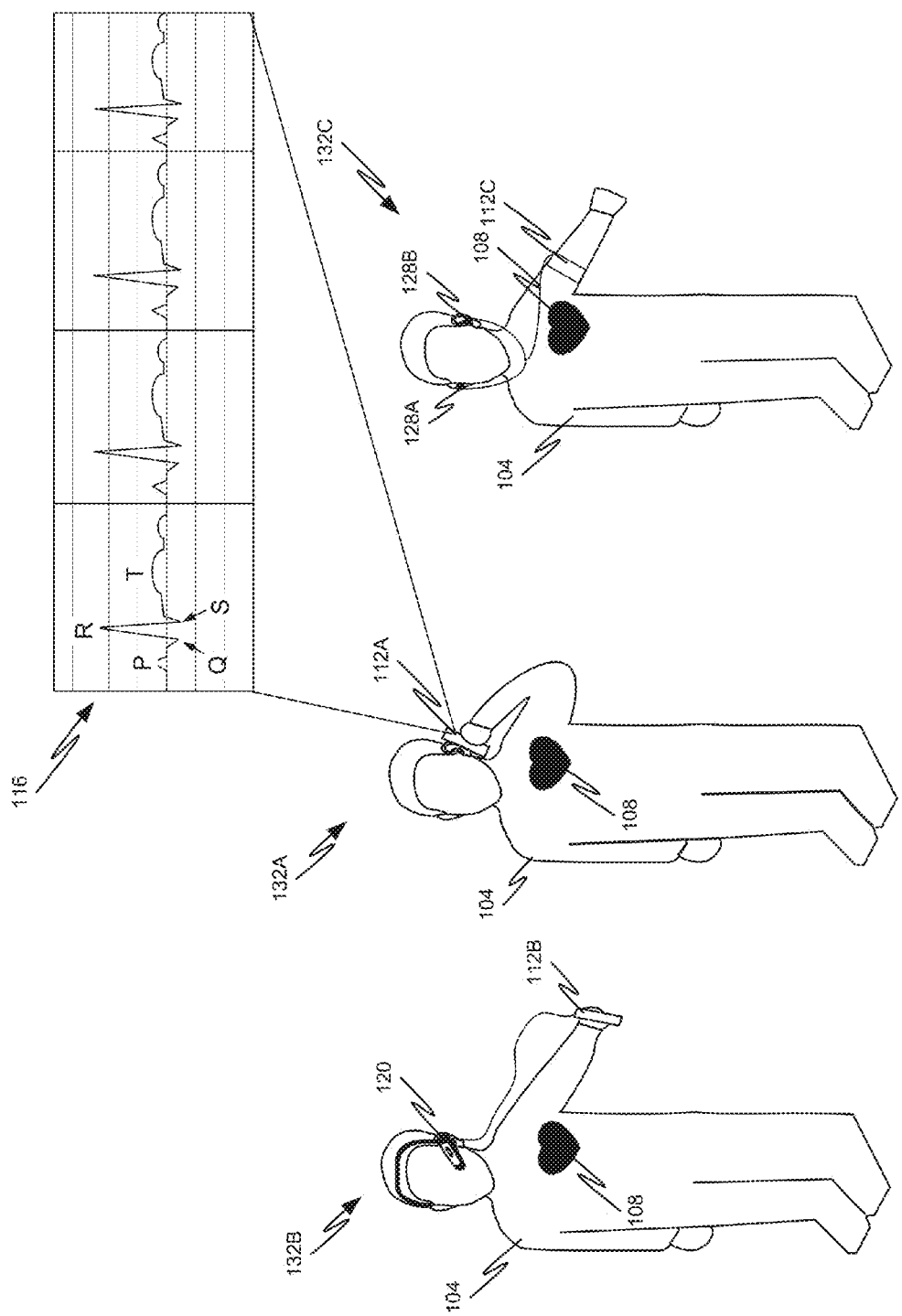
FIG. 1 is a system diagram of a personal electronic device unobtrusively detecting a heart rate signal in accordance with an exemplary embodiment of the present disclosure.

FIG. 1 shows a personal electronic device 112 that unobtrusively monitors the heart rate and heart rhythms of a user 104. An electrocardiogram (EKG) measures small differential voltages using electrodes contacting a patient's skin, to view the electrical behavior, or electrical characteristics, of the heart muscle. Stated another way, an EKG is a recording of a waveform(s)) or heart signal that reflects the electrical activity of the heart. As shown in FIG. 1, the personal electronic device 112 may unobtrusively detect a typical heart signal 116. Heart signal 116 represents a typical cardiac cycle waveform of a normal heartbeat. The voltages produced represent pressures exerted by the heart muscles in one pumping cycle. For example, the first upward deflection, P, is due to atria contraction and is known as the atrial complex. The other deflections, Q, R, S, and T, are all due to the action of the ventricles and are known as the ventricular complexes. Each time that this signal is present, a heartbeat is generated. By detecting the Q, R, and S deflections, otherwise known as the QRS complex, and measuring the time that elapses between adjacent QRS complexes, heart rate and rhythm irregularities may be detected. Any detected heart rate and rhythm irregularities may be indicative of a possible heart disorder.

Embodiments in accordance with the present invention detect and then monitor the heart signal 116 generated by the heart 108 of a user 104 for heart rate and rhythm anomalies. In some embodiments, the personal electronic device 112A capable of monitoring a user's 104 heart rate and rhythm for anomalies may be implemented in a handset of a telephone such that an electrode is placed on the earpiece of a wired or wireless handset of a telephone and a second electrode is placed in a location where the user's 104 hand comes in contact with the handset, such as in configuration 132A. Specifically, a user's 104 ear may contact the electrode placed on the earpiece of the handset of the telephone while the user's 104 hand (in this instance, the user's left hand) may contact the electrode placed on the handset. Assuming the user's 104 ear contacts the electrode placed on the earpiece and the user's 104 hand contacts the electrode placed on the handset, QRS complexes of a user's 104 heart signal 116 may be detected. By measuring the elapsed time between adjacent QRS complexes, one or more heart rate and rhythm irregularities associated with a user's 104 heart 108 may be detected.

The electrode placement of configuration 132A is considered unobtrusive, as the location of electrodes on the personal electronic device 112A are positioned in a manner such that the user 104 contacts at least two electrodes when using the personal electronic device 112A for its intended or primary purpose—in this instance a communicating. Moreover, when both electrodes are contacting the user 104 as the user 104 is using the personal electronic device 112A, the detection, recording, and analysis of the user's heart rate and heart rhythm occurs in an unobtrusive manner. That is, the monitoring of a user's 104 heart rate and rhythm is implemented in a device that is consciously being used for a function other than EKG monitoring, such as the participation in a communication session (e.g. making a phone call).

In another embodiment, the personal electronic device 112B capable of unobtrusively monitoring a user's 104 heart rate and rhythm may be configured such that a headset 120 includes at least one electrode while the personal electronic device 112B includes a second electrode, as shown in configuration 132B. Such a configuration 132B may be consistent with user listening to music or watching videos on the personal electronic communication device 112B. Specifically, a user's 104 ear may contact an electrode placed on and/or around the headset 120 while the user's 104 hand (in this instance, the user's left hand) may contact an electrode placed on the personal electronic device 112B. Assuming the user's 104 ear contacts the electrode placed on and/or around the headset 120 and the user's 104 hand contacts the electrode placed on the personal electronic device 112B, a QRS complex of a user's 104 heart signal 116 may be detected. By measuring the elapsed time between adjacent QRS complexes, one or more heart rate and rhythm irregularities associated with a user's 104 heart 108 may be detected.

The electrode placement of configuration 132B is considered unobtrusive, as the location of electrodes on the personal electronic device 112B are positioned in a manner such that the user 104 contacts at least two electrodes when using the personal electronic device 112B for its intended or primary purpose—in this instance watching videos and/or listening to music. Moreover, when both electrodes are contacting the user 104, such as when the user 104 is using the personal electronic device 112B, the detection, recording, and analysis of the user's heart rate and heart rhythm occurs in an unobtrusive manner. That is, the monitoring of a user's 104 heart rate and rhythm is implemented in a device that is consciously being used for a function other than EKG monitoring, such as listening to music and/or watching videos.

In another embodiment, the personal electronic device 112C for unobtrusively monitoring a user's 104 heart rate and rhythm may be configured such that at least one ear bud 128 includes at least one electrode white the personal electronic device 112C includes a second electrode, as shown in configuration 132C. Such a configuration 132C may be consistent with the personal electronic device 112C being held against a user's 104 arm with an elastic band (a common location when people are engaged in physical activity). Specifically, a user's 104 ear may contact an electrode placed on and/or around at least one of the ear buds 128A and/or 128B, while the user's 104 arm (in this instance, the user's left arm) may contact an electrode placed on the personal electronic device 112C. Assuming the user's 104 ear contacts the electrode placed on and/or around at least one ear bud 128 and the user's 104 arm contacts the electrode placed on the personal electronic device 112C, a QRS complex of a user's 104 heart signal 116 may be detected. By measuring the elapsed time between adjacent QRS complexes, one or more heart rate and rhythm irregularities associated with a user's 104 heart 108 may be detected.

The electrode placement of configuration 132C is considered unobtrusive, as the location of electrodes on the personal electronic device 112C are positioned in a manner such that the user 104 contacts at least two electrodes when using the personal electronic device 112C for its intended or primary purpose—in this instance listening to audio. Moreover, when both electrodes are contacting the user 104, such as when the user 104 is using the personal electronic device 112C, the detection, recording, and analysis of the user's heart rate and heart rhythm occurs in an unobtrusive manner. That is, the monitoring of a user's 104 heart rate and rhythm is implemented in a device that is consciously being used for a function other than EKG monitoring, such as listening to audio.

Of course, additional configurations 132 may be realized where the monitoring of a user's 104 heart rate and rhythm is implemented in an unobtrusive manner. For instance, the personal electronic device 112 may be located on a user's 104 belt and an electrode of the personal electronic device 112 may contact the skin of the user 104. In some embodiments and consistent with the present disclosure, physical contact may not be required between the electrode and the user's 104 skin as an electrode may be of the capacitively coupled noncontact electrode type. In such an instance, the electrode may be able to detect a heart signal 1116 through clothing. Additional configurations 132 may include instances where the personal electronic device 112 is located in a user's 104 pocket, located in user's 104 right hand or other limb, and/or in contact with user 104 in some other manner.

Figure 2:
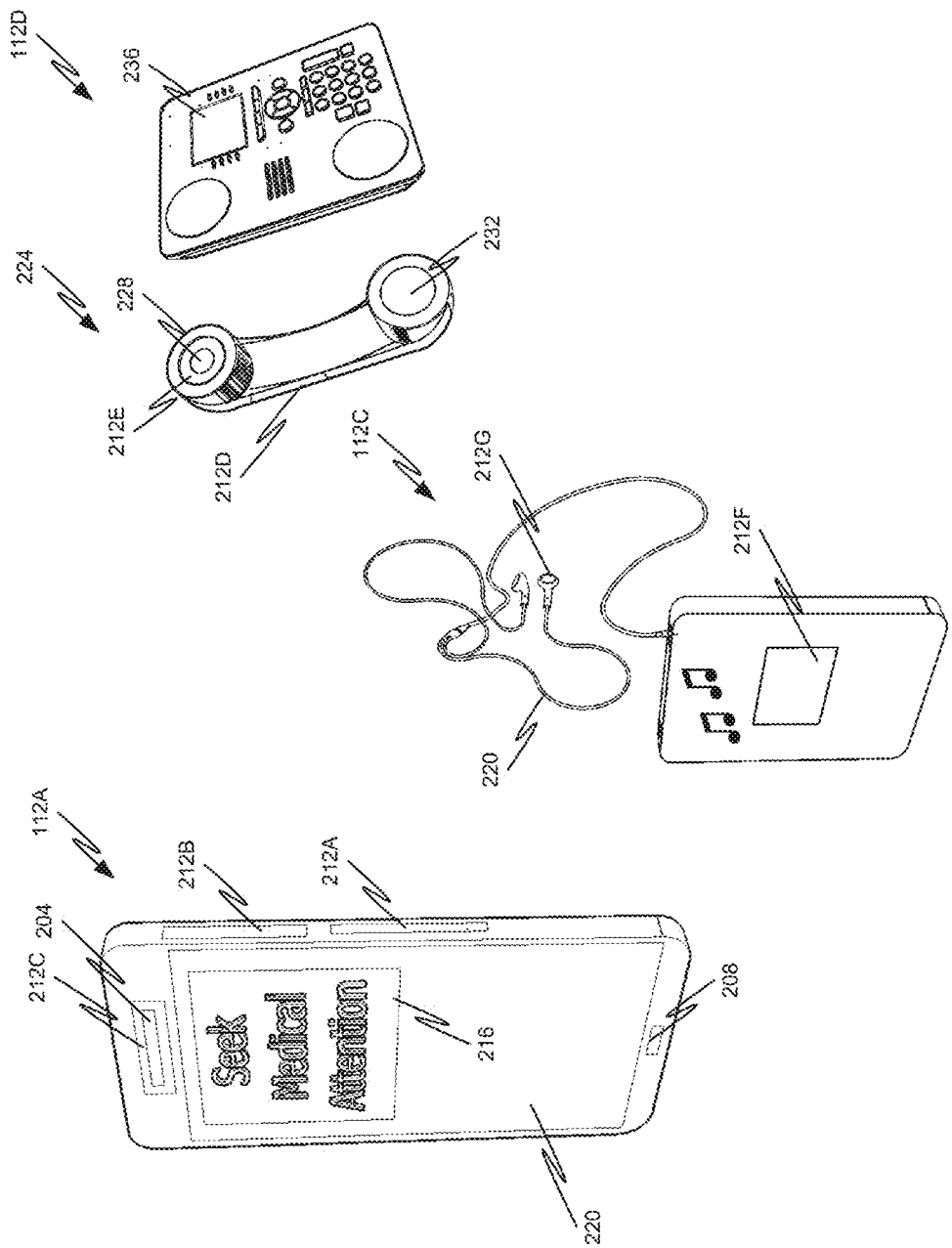
FIG. 2 illustrates various personal electronic devices capable of unobtrusively monitoring a user's EKG.

Referring now to FIG. 2, various personal electronic devices 112 are shown which provide unobtrusive monitoring of a user's 104 heart rate and rhythm for anomalies. For example, personal electronic device 112A illustrates a telephone handset having an electrode 212C located in the vicinity of a headset speaker 204, an electrode 212A and/or 212B located on the handset 112A, microphone 208, and a informational message 216 displayed on a display 220 of handset 112A. For instance, while a user 104 is using personal electronic device 112A for its intended and/or primary purpose, the electrode 212C may be in contact with the user's 104 ear and one or more of electrodes 212A/B may be in contact with the user's 104 hand. Thus, the electrodes 212 are operable to detect the QRS complex of a user's 104 heart signal 116. It is important to note that the electrode 212C in the vicinity of a headset speaker 204 is operable to contact a user's 104 ear when the user 104 is using the personal electronic device 112A in its intended manner and/or for its intended function. Additionally, the one or more electrodes 212A/212B are operable to contact a user's 104 hand, arm, limb or otherwise when the user 104 is using the personal electronic device 112A in its intended manner. Thus, the user 104 does not have to hold, touch, or come into contact with the personal electronic device 112A in a manner that is inconsistent with the manner for which device 112A is intended. That is, the user 104 holds, touches, and/or comes into contact with the personal electronic device 112A in a manner to utilize a function other than EKG monitoring, like communicating with another user. That is, the primary function of a telephone handset is to communicate with another user. Therefore, the detection and analysis of the user's 104 heart signal is unobtrusive.

As another example, a personal electronic device 112C illustrates a music player having an electrode 212G located on and/or around an ear bud or a set of ear buds 220, and an electrode 212F located on the music player 112C. For instance, while a user 104 is using personal electronic communication device 112C for its intended and/or primary purpose, the electrode 212G may be in contact with the user's 104 ear and electrodes 212F may be in contact with the user's 104 hand, arm, limb or otherwise. Thus, the electrodes 212 are operable to detect the QRS complex of a user's 104 heart signal 116. It is important to note that the electrode 212G as part of the ear bud 220 is operable to contact a user's 104 ear when the user 104 is using the personal electronic device 112F and ear buds 220 in their intended manner and/or for their intended function, such as listening to music. Additionally, the electrode 212F are operable to contact a user's 104 hand, arm, limb or otherwise when the user 104 is using the personal electronic device 112C in its intended manner. Thus, the user 104 does not have to hold, touch, or come into contact with the personal electronic device 112C in a manner that is inconsistent with the manner for which device 112C is intended. That is, the user 104 holds, touches, and/or comes into contact with the personal electronic device 112C in a manner to utilize a function other than EKG monitoring, like listening to music. That is, the primary function of a music playing device is to play music. Therefore, the detection and analysis of the user's 104 heart signal is unobtrusive.

Further, as another example, personal electronic device 112D illustrates a telephone handset 224 having an electrode 212E located in the vicinity of an earpiece or handset speaker 228, an electrode 212D located on the handset 224, microphone 232, and a display 236 that may display an informational message. For instance, while a user 104 is using personal electronic communication device 112D for its intended and/or primary purpose, the electrode 212E may be in contact with the user's 104 ear and the electrode 212D may be in contact with the user's 104 hand. Thus, the sensor contacts 212 become operable and the QRS complex of a user's 104 heart signal 116 may be detected. It is additionally important to note that the electrode 212E in the vicinity of a headset and/or speaker 228 is operable to contact a user's 104 ear when the user 104 is using the personal electronic device 112D in its intended manner and/or for its intended function. Additionally, the electrode 212D is operable to contact a user's 104 hand, arm, and/or limb when the user 104 is using the personal electronic device 112D in its intended manner. Thus, the user 104 does not have to hold, touch, or come into contact with the personal electronic device 112D in a manner that is inconsistent with the manner for which device 112D is intended. That is, the user 104 holds, touches, and/or comes into contact with the personal electronic device 112D in a manner to utilize a function other than EKG monitoring, like communicating with another user. That is, the primary function of a telephone is to communicate with another user. Therefore, the detection and analysis of the user's 104 heart signal is unobtrusive.

Figure 3:
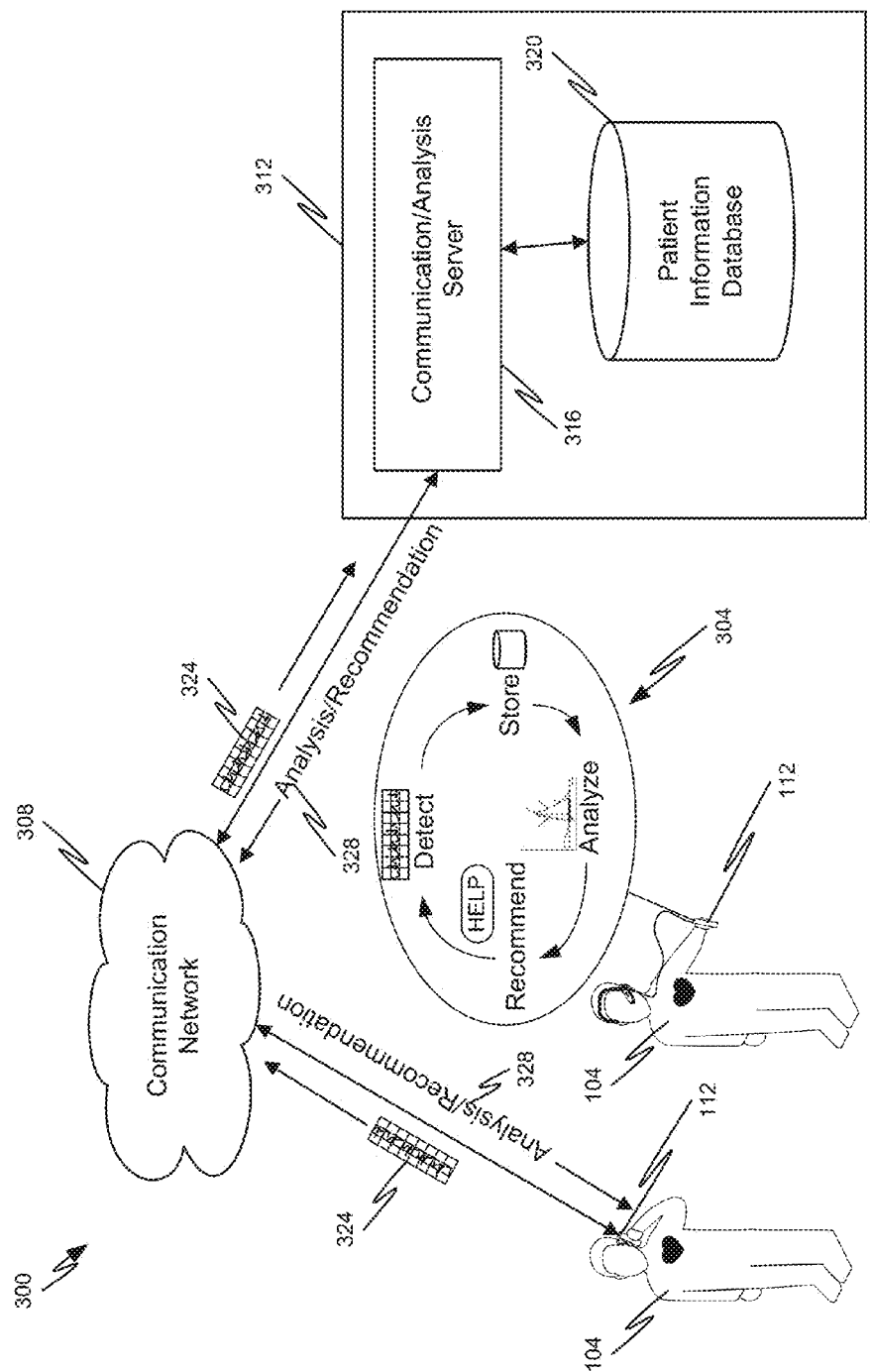
FIG. 3 illustrates a representative configuration for unobtrusively monitoring an EKG of a user.

FIG. 3 shows an illustrative embodiment of an unobtrusive monitoring system 300 for monitoring a user's 1104 heart rate and rhythm in accordance with at least some embodiments of the present disclosure. The unobtrusive monitoring system 300 may comprise a personal electronic communication device 112 for monitoring a user's 104 heart rate and rhythm for anomalies in an unobtrusive manner. For example, and as described below, a user's ear may contact an electrode, such as electrode placed on and/or around a headset 120, while the user's hand may contact an electrode placed on the personal electronic device 112. Upon such contact, the electrodes may become operable and the QRS complex of a user's 104 heart signal 116 may be detected. Thus, the personal electronic device 112 may perform the heart rate and rhythm monitoring steps of 304 comprising unobtrusively detecting the user's 104 heart signal, storing the user's 104 heart signal, analyzing the user's 104 heart signal, and providing a recommendation, if any, to the user 104. That is, the personal electronic device 112 performs all unobtrusive heart rate and rhythm monitoring steps 304 locally in addition to performing unrelated and common functions other than EKG monitoring, such as listening to music or watching videos.

In some embodiments, the personal electronic device 112 may include a telecommunication function allowing the personal electronic device 112 to communicate using a communication network 308. Although the personal electronic device 112 may perform unobtrusive heart rate and rhythm monitoring steps 304 locally, the personal electronic device 112 may additionally and unobtrusively detect a user's 104 heart rate and rhythm and further augment any processing, analysis, and/or recommendations associated with the detected heart rate and rhythm utilizing a communication/analysis server 316. For example, the personal electronic device 112 may unobtrusively detect a user's 104 heart signal 116 as previously described. The unobtrusively detected heart signal 116 may then be stored locally as cardiac information 324 at the personal electronic device 112 and/or transmitted to the communication/analysis server 316 via the communication network 308. The transmitted cardiac information 324 may be received at communication/ analysis server 316 and stored in a patient information database 320. The cardiac information 324 may comprise raw signal data corresponding to a user's 104 heart signal 116. Alternatively, or in addition, the cardiac information 324 may comprise processed signal data corresponding to a user's 104 heart signal 116; such processed information may include heart rate and QRS specific information.

As one example, the communication/analysis server 316 may reside at a monitoring site 312, such as at a hospital, health records collection site, Public Safety Answering Point (PSAP), healthcare provider, or the like. The communication/analysis server 316 may process, or further process, and analyze the received cardiac information 324 and generate one or more analyses/recommendations 328 based on the processed cardiac information. The generated analyses/recommendations 328 may then be transmitted to the personal electronic device 112 such that a user is informed, if necessary, of any detected heart rate and/or heart rhythm anomalies and/or recommendations. Alternatively, or in addition, the cardiac information 324 and the one or more analyses/recommendations 328 based on the processed cardiac information may be stored at the patient information database 320. In some embodiments, the patient information database may reside within the monitoring site 312, within the communication/analysis server 316, and/or external to the monitoring site 312. For example, the patient information database 320 may be in communication with, either directly or indirectly, the communication network 308. The patient information database 320 may include additional information pertaining to one or more users 104. For example, a history of cardiac information 324, history of analyses/recommendations 328, medical information associated with the user 104, and the like may be stored and later accessible in the patient information database 320 by the user 104 and/or healthcare providers.

In accordance with embodiments of the present invention, the communication network 308 may be packet-switched and/or circuit-switched. An illustrative communication network 308 includes, without limitation, a Wide Area Network (WAN), such as the Internet, a Local Area Network (LAN), a Personal Area Network (PAN), a Public Switched Telephone Network (PSTN), a Plain Old Telephone Service (POTS) network, a cellular communications network, an IP Multimedia Subsystem (IMS) network, a Voice over IP (VoIP) network, a SIP network, a Wi-Fi® network, a Bluetooth®, or combinations thereof. The Internet is an example of the communication network 308 that constitutes an Internet Protocol (IP) network including many computers, computing networks, and other communication devices located all over the world, which are connected through many telephone systems and other means. In one configuration, the communication network 308 is a public network supporting the TCP/IP suite of protocols, Communications supported by the communication network 308 include real-time, near-real-time, and non-real-time communications. For instance, the communication network 308 may support voice, video, text, web-conferencing, cardiac information, and/or any combination of media. Moreover, the communication network 308 may comprise a number of different communication media such as coaxial cable, copper cable/ wire, fiber-optic cable, antennas for transmitting/receiving wireless messages, and combinations thereof. In addition, it can be appreciated that the communication network 308 need not be limited to any one network type, and instead may be comprised of a number of different networks and/or network types.

Figure 4:
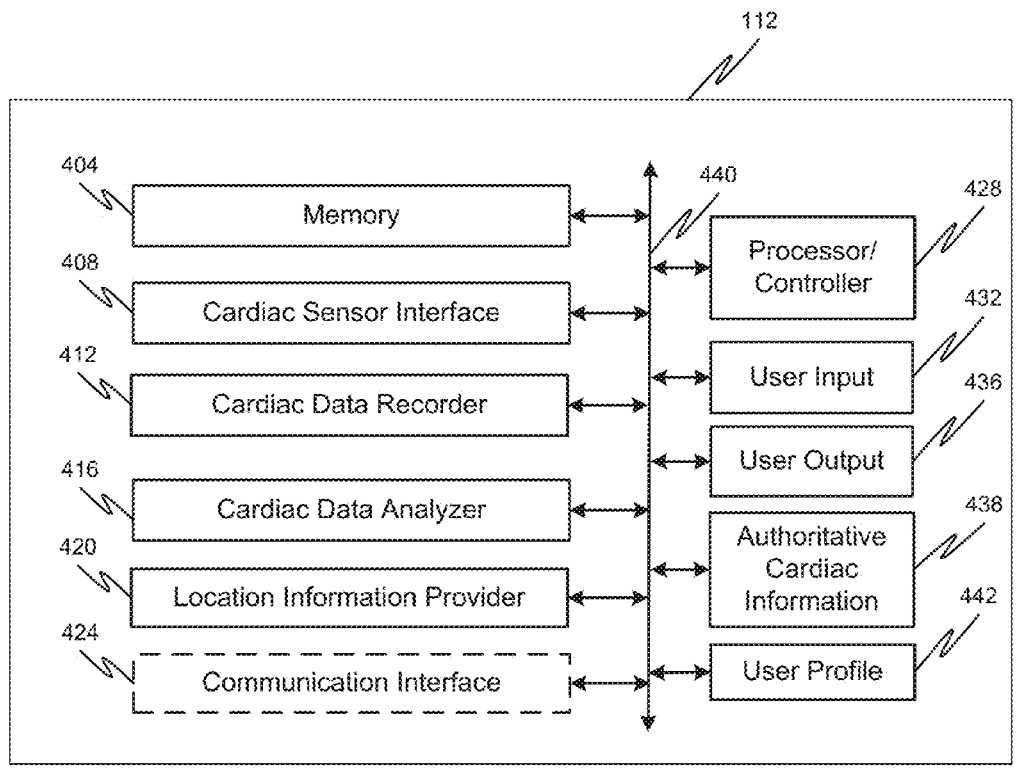
FIG. 4 is a block diagram of a personal electronic device in accordance with an exemplary embodiment of the present disclosure.

FIG. 4 illustrates a block diagram depicting one or more components of a personal electronic device 112. The personal electronic device 112 may include a processor/controller 424 capable of executing program instructions. The processor/controller 428 may include any general purpose programmable processor or controller for executing application programming. Alternatively, or in addition, the processor/controller 428 may comprise an application specific integrated circuit (ASIC). The processor/controller 428 generally functions to execute programming code that implements various functions performed by the personal electronic device 112 in accordance with at least some embodiments of the present disclosure.

The personal electronic device 112 may additionally include memory 404. The memory 404 may be used in connection with the execution of programming instructions by the processor/controller 428, and for the temporary or long term storage of data and/or program instructions. For example, the processor/controller 428, in conjunction with the memory 404 of the personal electronic device 112, may implement unobtrusive heart rate and rhythm monitoring, cardiac information processing, applications, and web services that are used to access one or more monitoring sites 312.

The memory 404 of the personal electronic device 112 may comprise solid state memory that is resident, removable and/or remote in nature, such as DRAM and SDRAM. Moreover, the memory 404 may comprise a plurality of discrete components of different types and/or a plurality of logical partitions. In accordance with stilt other embodiments, the memory 404 comprises a non-transitory computer readable storage medium. Such a medium may take many forms, including but not limited to, non-volatile media, volatile media, and transmission media.

The memory 404 of the personal electronic device 112 may further be operable to store heart rate, heart rhythm, and/or cardiac information associated with user 104. Specifically, personal electronic device 112 may include one or more cardiac sensor interfaces 408. The cardiac sensor interface 408 may be the same or similar to the electrodes contacting a user's 104 skin to measure small differential voltages to view the electrical behavior, or electrical characteristics, of the heart muscle. For example, the cardiac sensor interface 408 may correspond to or otherwise be associated with an electrode 212C placed in the vicinity of a handset speaker 204 of a personal electronic device 112A. Further, the cardiac sensor interface 408 may correspond to or otherwise be associated with an electrode 212A located on the side of a personal electronic device 112A. Generally, the cardiac sensor interface 408 and/or the associated electrode is in contact with a user and acquires the user's 104 heart signal 116.

In some embodiments, the cardiac sensor interface 408 may become operable only when two or more cardiac sensor interfaces 408 and/or the associated electrodes are in contact with a user's 104 skin. Therefore, the personal electronic device 112 does not receive or attempt to receive a user's 104 heart signal 116 unless two or more cardiac sensor interfaces 408 and/or the associated electrodes are in contact with a user's 104 skin. Additionally, the differential voltages received may be processed, filtered, amplified, or otherwise altered to better detect a QRS complex and an elapsed time, and/or distance, between adjacent QRS complexes. Such filtering may occur at the cardiac sensor interface 408. In some embodiments, the cardiac sensor interface 408 may also tag or otherwise add electrode/sensor type information to the detected signal. For example, a cardiac sensor interface 408 comprising an electrode located in an ear bud 128 may require a different amplification, processing, and/or filtering algorithm than an electrode located on a handset.

The personal electronic device 112 may further include user input devices 432 and user output devices 436 to be used in connection with the personal electronic device 112. For example, the user 104 may enter information, and/or make a selection using user input device 432. Other examples of user input devices 432 include a keyboard, a numeric keypad, a touch screen, a microphone, scanner, and pointing device combined with a screen or other position encoder. Examples of user output devices 436 include a display, a touch screen display, a speaker, a printer, and a tactile feedback component that provides tactile feedback using for example, vibration, heat, electrical, or any other type of feedback. The personal electronic device 112 may include a communication interface 424 to allow for communication between the personal electronic device 112 and the communication/analysis server 316. The communication interface 424 may support 3G, 4G, cellular, Wi-Fi®, Bluetooth®, NFC, RS232, and RF and the like. In some embodiments, the communication interface 424 may provide one or more means for sending cardiac information 324 to and/or retrieving analyses/recommendations 328 from the communication/analysis server 316. As another example, the communication interface 424 may provide one or more means for retrieving cardiac information from the personal electronic device 112. For example, a person or first responder may be able to interrogate, access and/or retrieve cardiac information data from a user's 104 personal electronic device 112 utilizing the communication interface 424.

The personal electronic device may further include a cardiac data recorder 412 that records or otherwise stores the user's 104 heart signal 116 and information associated therewith. The cardiac data recorder 412 may store the user's 104 heart signal 116 and information associated therewith to or within memory 404. The cardiac data analyzer 416 may then retrieve one or more pieces of stored information from the cardiac data recorder 412. For example, the cardiac data analyzer 416 may retrieve one or more previously stored QRS complexes for a user 104. The retrieved one or more QRS complexes may then be analyzed, and/or further processed, by the cardiac data analyzer 416 to locate, or otherwise determine, possible heart rate and/or heart rhythm anomalies. As another example, the cardiac data analyzer 416 may retrieve one or more heart rate signals 116 for a specific time period from the cardiac data recorder 412. The cardiac data analyzer 416 may then process the retrieved heart rate signal 116 to determine one or more values associated with a QRS complex, such as a duration between an adjacent QRS complex and/or duration of the QRS complex. These determined values associated with one or more QRS complexes may then be compared to known parameters indicating cardiac anomalies and/or non-cardiac anomalies. For example, atrial fibrillation may be detected when coarse and/or fine fibrillation is present and/or when the ventricular response (QRS) is irregular, slow, or rapid. Moreover, in instances where a P wave is detectable, the absence of a P wave may be indicative of atrial fibrillation. As another example, two p waves followed by one QRS may indicate the presence of atrial flutter. As another example, a duration of a QRS complex that is greater than a threshold, for example 0.10 seconds, may indicate a heart anomaly. Based on the detection of and/or non-detection of a heart rate and/or rhythm anomaly, the cardiac data analyzer 416 may provide such analyses and/or a recommendation to the user.

Additionally, the cardiac data analyzer 416 may compare a user's heart signal 116 and information associated therewith to an authoritative information source to determine whether the heart signal 116 is normal for the user. For example, the cardiac data analyzer 416 may retrieve from or otherwise consult an authoritative source of cardiac information, such as a medical database, to obtain heart rate and/or heart rhythm information comprising trends, patterns, and/or parameters that are specific to the user. This authoritative information may be stored as authoritative cardiac information 438 located at the personal electronic device 112. Alternatively, or in addition, the authoritative information may be accessible via the communication interface 424 and/or the authoritative cardiac information 438 may be updated via authoritative information accessible via communication interface 424. This authoritative information may be based on a user profile 442 created and maintained at the personal electronic device 112, a user profile at a patient information database 320, or the like.

The user profile 442 may contain user specific and user relevant information, such as age, activity, fitness level etc. . . . such that information retrieved from the authoritative source of information is specific and relevant to the user. As one example, an authoritative data source may provide an upper heart rate parameter, a lower heart rate parameter, patterns, trends, or combinations thereof that are specific to a user's age and activity information. The cardiac data analyzer 416 may then compare the user's heart signal 116 to such authoritative information to determine whether the heart signal 116 is normal for the user. For instance, the cardiac data analyzer 416 may determine that a resting heart rate of 50 is normal for a distance runner of age of 35; however, the cardiac data analyzer 416 may determine that a resting heart rate of 50 for a person of age 80 is not normal.

Moreover, the user's user profile 442 may include historical information for a user; such historical information may include user specific historical heart rates, user specific historical heart rhythms, and any trends, patterns, and the like derived from the user specific historical information. The cardiac data analyzer 416 may compare the user's heart rate signal 116 to user specific historical information, trends, patterns, and the like to determine if the user's heart rate signal 116 is normal. For instance, over time and as a result of physical activity, a user's resting heart rate may slowly decrease; such trend and/or pattern may be used when determining whether the user's heart rate is normal.

The result of the cardiac data analyzer 416 may then be used to provide an indication of the analyses and/or a recommendation to the user. For example, the cardiac data analyzer 416 may provide an indication to user output 432 alerting the user to a low detected heart rate, abnormal rhythm, and/or the like; such an alert may also include one or more recommendations, such as "Seek Medical Attention". Alternatively, or in addition, the cardiac data analyzer 416 may notify a health care provider of the detected anomaly. For example, a health care provider may be notified by a text message, email, phone call or the like; such notification may include the anomaly detected, an anomaly history, a heart rate and/or rhythm history, and any notifications that may have been provided to the user.

In some embodiments, the personal electronic device 112 may further include a location information provider 420. The location information provider 420 may provide location information related to the cardiac sensor interface 408 and/or one or more electrodes. For instance, the position of and/or location of an electrode contacting a user's 104 body may provide one or more views, or angles, of a user's 104 heart 108. Different views may provide additional opportunities for analyzing a user's 104 heart signal 116 at the cardiac data analyzer 416. The memory 404, cardiac sensor interface 408, cardiac data recorder 412, cardiac data analyzer 416, location information provider 420, communication interface 424, processor/controller 428, user input 432, user output 436, and authoritative/historical cardiac information 438 may all communicate using a bus 440.

Figure 5:
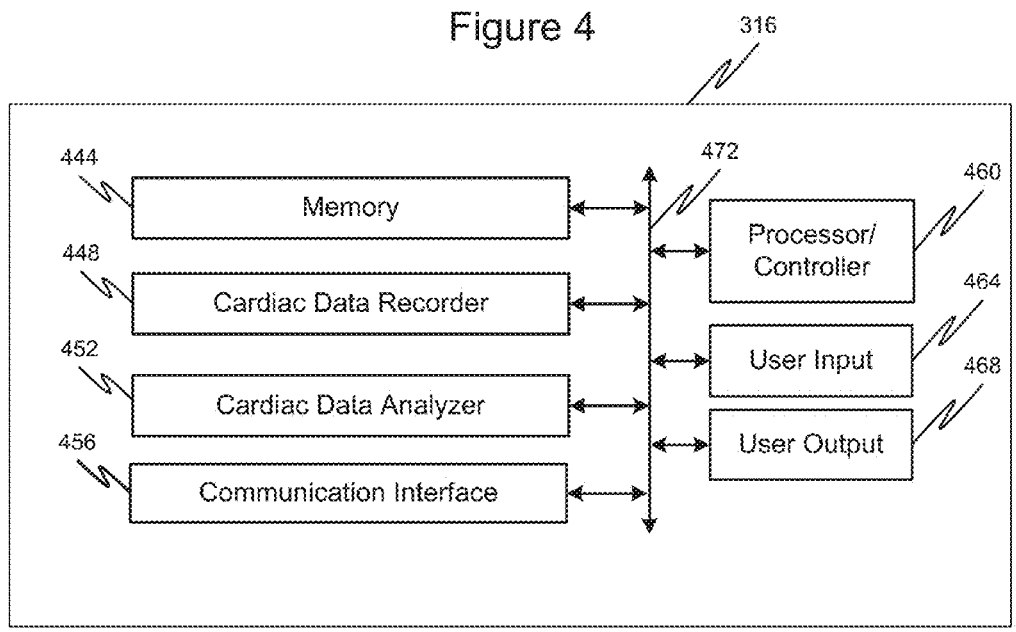
FIG. 5 is a block diagram of a communication/analysis server in accordance with an exemplary embodiment of the present disclosure.

FIG. 5 illustrates a block diagram depicting one or more components of a communication/analysis server 316. The communication/analysis server 316 may include a processor/controller 460 capable of executing program instructions. The processor/controller 460 may include any general purpose programmable processor or controller for executing application programming. Alternatively, or in addition, the processor/controller 460 may comprise an application specific integrated circuit (ASIC). The processor/controller 460 generally functions to execute programming code that implements various functions performed by the communication/analysis server 316 in accordance with at least some embodiments of the present disclosure.

The communication/analysis server 316 may additionally include memory 444. The memory 444 may be used in connection with the execution of programming instructions by the processor/controller 460, and for the temporary or long term storage of data and/or program instructions. For example, the processor/controller 460, in conjunction with the memory 444 of the communication/analysis server 316, may implement unobtrusive heart rate and rhythm monitoring, cardiac information processing, applications, and web services that are used to with one or more personal electronic devices 112.

The memory 444 of the communication/analysis server 316 may comprise solid state memory that is resident, removable and/or remote in nature, such as DRAM and SDRAM. Moreover, the memory 444 may comprise a plurality of discrete components of different types and/or a plurality of logical partitions. In accordance with still other embodiments, the memory 444 comprises a non-transitory computer readable storage medium. Such a medium may take many forms, including but not limited to, non-volatile media, volatile media, and transmission media.

The memory 444 of the communication/analysis server 316 may further be operable to store heart rate, heart rhythm, and/or cardiac information associated with a user 104. The communication/analysis server 316 may also include one or more user input devices 464 and user output devices 468 to be used in connection with the communication/analysis server 316. The communication/analysis server 316 may include a communication interface 456 to allow for communication between a personal electronic device 112 and the communication/analysis server 316. The communication interface 456 may support 3G, 4G, cellular, WiFi, Bluetooth®, NFC, RS232, and RF and the like. In some embodiments, the communication interface 456 may provide one or more means for receiving cardiac information 324 and/or sending, or transmitting, analyses/recommendations 328 to the personal electronic device 112.

Similar to the personal electronic device, the communication/analysis server 316 may further include a cardiac data recorder 448 that records or otherwise stores the user's 104 heart signal 116 and information associated therewith. The cardiac data recorder 448 may store the user's 104 heart signal 116 and information associated therewith to or within memory 444. The cardiac data analyzer 452 may then retrieve one or more pieces of stored information from the cardiac data recorder 448. For example, the cardiac data analyzer 452 may retrieve one or more previously stored QRS complexes for a user 104. The retrieved one or more QRS complexes may then be analyzed, and/or further processed, by the cardiac data analyzer 452 in a similar manner as described with respect to the cardiac data analyzer 416 of the personal electronic device 112. The memory 444, cardiac data recorder 448, cardiac data analyzer 452, communication interface 456, processor/controller 460, user input 464, and user output 468 may all communicate using a bus 472.

Figure 6:
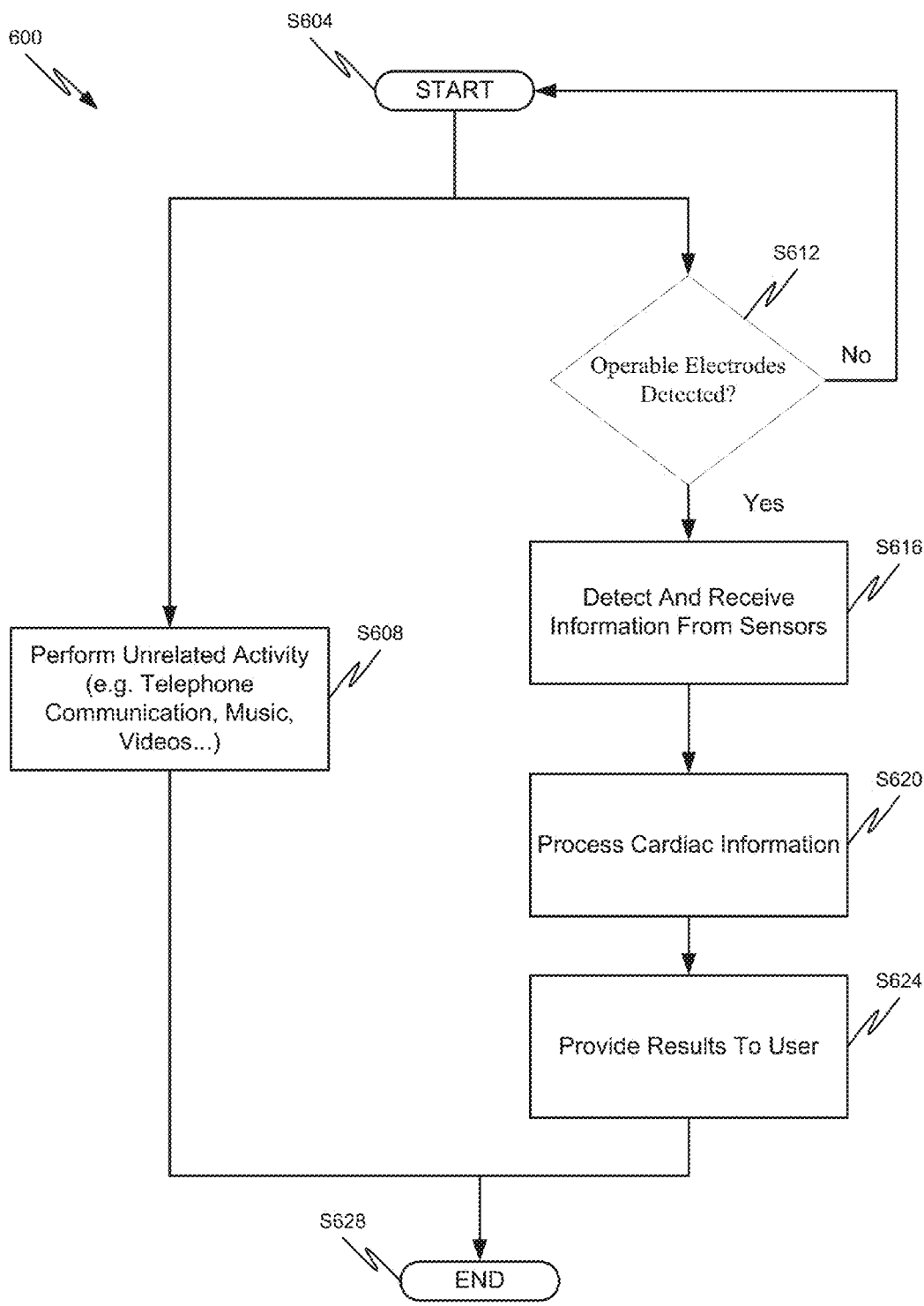
FIG. 6 is a flow diagram depicting a method associated with a personal electronic device in accordance with an exemplary embodiment of the present disclosure.

Referring now to FIG. 6, a method 600 of performing unobtrusive heart rate and rhythm monitoring will be discussed in accordance with embodiments of the present disclosure. Method 600 is in embodiments, performed by a device, such as a personal electronic device 112. More specifically, one or more hardware and software components may be involved in performing method 600. In one embodiment, one or more of the previously described modules and/or devices perform one or more of the steps of method 600. The method 600 may be executed as a set of computer-executable instructions executed by a computer system or personal electronic device and encoded or stored on a computer-readable medium. Hereinafter, the method 600 shall be explained with reference to systems, components, modules, software, etc. described with FIGS. 1-5.

Method 600 may continuously flow in a loop, flow according to a timed event, or flow according to a change in an operating or status parameter. Method 600 is initiated at step S604 where a personal electronic device 112 may start one or more user initiate functions. For example, a user 104 may initiate a function such that music is played. Alternatively, or in addition, a user 104 may initiate a function such that a communication session is initiated and/or established. At step 608, a personal electronic device 112 may perform such initiated activity. For example, the personal electronic device 112 may play music, initiate and establish a communication, play a video, and/or the like. Importantly, the function, and/or activity performed at step S608 is unrelated to the detection, processing, and analysis of the user's 104 heart rate and/or heart rhythm.

As the activity is performed at step S608, the method also proceeds to step S612 where the personal electronic device 112 determines whether operable electrodes are detected. Operable electrodes may correspond to electrodes that are in contact with a user's skin. As one example, if operable electrodes are not detected, such as if a user is not holding a personal electronic device 112 or the manner in which the user 104 is holding the personal electronic device 112 does not lend itself to heart rate and/or heart rhythm detection, the Method 600 may proceed back to step S604. If, operable electrodes are detected at step S612, the Method 600 proceeds to step S616 where the electrodes of the personal electronic device 112 detect and receive electrical information from the electrodes. For example, electrodes associated with the cardiac sensor interface 408 may detect the existence of differential voltages between two or more electrodes corresponding to a heart rate signal 116. Such detected voltages may be amplified, filtered, and converted into a digital representation. The detected heart rate signal 116 may then be stored by the cardiac data recorder 412. It is important to note that the detection of differential voltage signals may not be continuous. For example, the detected differential voltages may occur in only those instances where a user is in contact with two or more electrodes. The Method 600 may then proceed to step S620 where the heart rate signal 116 (e.g. cardiac information) is processed. Such processing at step S620 will be described in further detail with respect to FIG. 7 and FIG. 8. The processed cardiac information at step S620 may provide one or more results and/or recommendations; such results of the analyses and recommendations, if any, are then provided to the user at step S624. For example, if a heart anomaly is detected at step S620, a notification to seek medical attention may be provided to the user at step S624. Such notification may be displayed on a display of a personal electronic device 112, such as displaying a notification 215 on the display 220 of personal electronic device 112A. Alternatively, or in addition, a whisper tone or other low-volume announcement may be used to provide an audible notification to the user 104. The Method 600 then proceeds to step S628 where Method 600 ends.

Figure 7:
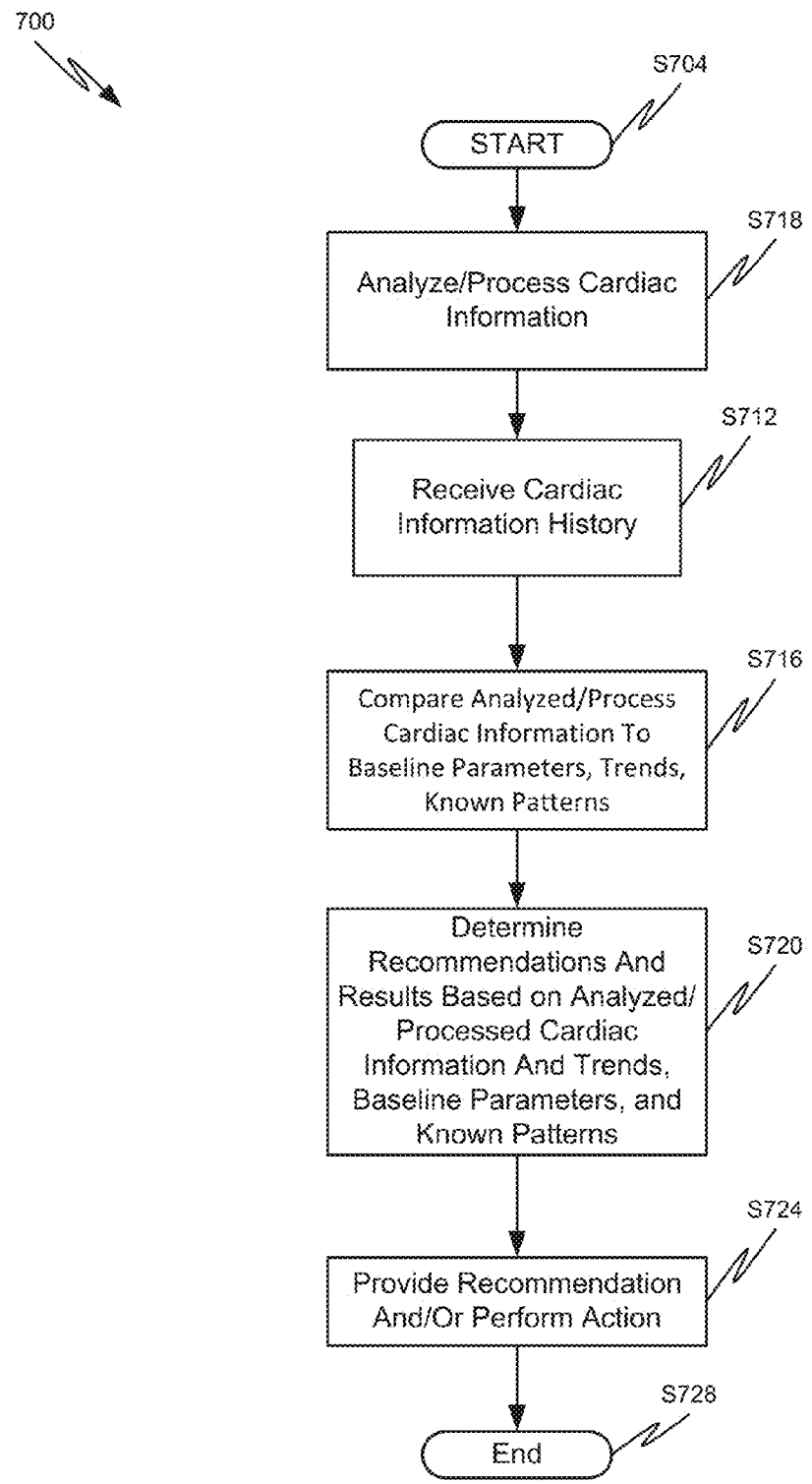
FIG. 7 is a flow diagram depicting a second method associated with a personal electronic device in accordance with an exemplary embodiment of the present disclosure.

Reaming now to FIG. 7, a method 700 for processing a detected heart signal 116 of a user 104 will be discussed in accordance with embodiments of the present disclosure. Method 700 is in embodiments, performed by a device, such as a personal electronic device 112. More specifically, one or more hardware and software components may be involved in performing method 700. In one embodiment, one or more of the previously described modules and/or devices perform one or more of the steps of method 700. The method 700 may be executed as a set of computer-executable instructions executed by a computer system or personal electronic device and encoded or stored on a computer-readable medium. Hereinafter, the method 700 shall be explained with reference to systems, components, modules, software, etc. described with FIGS. 1-6.

Method 700 may continuously flow in a loop, flow according to a timed event, or flow according to a change in an operating or status parameter. Method 700 is initiated at step S704 where a personal electronic device 112 may initiate the processing of a detected heart signal 116. As previously discussed, the unobtrusively detected heart signal 116 may be stored locally as cardiac information 324 at the personal electronic device 112. Therefore, the Method 700 may first retrieve any cardiac information 324 from the cardiac data recorder 412 and proceed to step S708, where the cardiac information is analyzed and processed. As previously discussed, the cardiac data analyzer 416 may be responsible for carrying out the analysis/processing of the cardiac information to locate, or otherwise determine, possible heart rate and/or heart rhythm anomalies.

As another example, at step S708, the analysis and processing may further include determining one or more values associated with a QRS complex of an unobtrusively detected heart rate signal. Such values may include, but are not limited to elapsed time between one or more adjacent QRS complexes, the duration of the QRS complex, and the absence and detectability of a P wave. Further, additional cardiac information history may be received at step S716. The additional cardiac information may comprise cardiac information history specific to the user 104 (e.g. additional cardiac information for a specified period of time), and/or may include baseline parameters, trends and any known patterns indicative of a heart rate and/or rhythm anomaly. Further, and as previously discussed, such additional cardiac information may include authoritative information from authoritative cardiac information 438 and/or user profile 432. At step S716, the analyzed and processed cardiac information, including any determined values associated with the QRS complex, such as the elapsed time between adjacent QRS complexes, may then be compared to the baseline parameters, trends, and known patterns received in step S712, daily. Method 700 then proceeds to step S720 where recommendations and/or results based on the analyzed and processed cardiac information and trends, baseline parameters, and known patterns are determined. For instance and as previously discussed, the previously determined values associated with the QRS complex may be compared to known parameters that are indicative of a cardiac anomaly. As one example, the QRS complexes may be detected at and may be occurring at irregular intervals; such irregular intervals may indicate atrial fibrillation. Based on the detected cardiac anomaly, a notification and/or action to be performed may be determined at step S720 that is specific to the detected anomaly. For example, if the detected cardiac information and/or heart signal 116 for a user 104 indicates that the QRS is irregular, slow, or rapid, a recommendation to seek medical attention for further testing may be determined.

Alternatively, or in addition, the personal electronic device 112 may alert health care providers to the anomaly detected by the cardiac data analyzer 416. In some embodiments, and depending on the anomaly detected, the personal electronic device 112 may even dial 9-1-1, though rare. The determination to alert health care providers may be specific to information in the user profile 442. For example, and as previously discussed, the cardiac data analyzer 416 may compare a user's heart signal 116 and information associate therewith to an authoritative information source to determine whether the heart signal 116 is normal for the user. For example, the cardiac data analyzer 416 may retrieve from or otherwise consult an authoritative source of cardiac information, such as a medical database, to obtain heart rate and/or heart rhythm information comprising trends, patterns, and/or parameters that are specific to the user. This authoritative information may be stored as authoritative cardiac information 438 located at the personal electronic device 112. This authoritative information may be based on a user profile 442 created and maintained at the personal electronic device 112, a user profile at a patient information database 320, or the like.

The user profile 442 may contain user specific and user relevant information, such as age, activity, fitness level etc., such that information retrieved from the authoritative source of information is specific and relevant to the user. As one example, an authoritative data source may provide an upper heart rate parameter, a lower heart rate parameter, patterns, trends, or combinations thereof that are specific to a user's age and activity information; this provided information may be consulted when determining whether or not to notify medical providers of a detected anomaly and/or call 9-1-1.

For instance, the cardiac data analyzer 416 may determine that a resting heart rate of 50 for a distance runner of age of 35 does not warrant a 9-1-1 call; however, the cardiac data analyzer 416 may determine that a resting heart rate of 50 for a person of age 80 does warrant a 9-1-1 call. Similarly, authoritative cardiac information and/or a user profile information may be consulted when detaining a notification. The determined notification may then be provided to the user at step S724. Method 700 then proceeds to step S728 where it ends.

Figure 8:
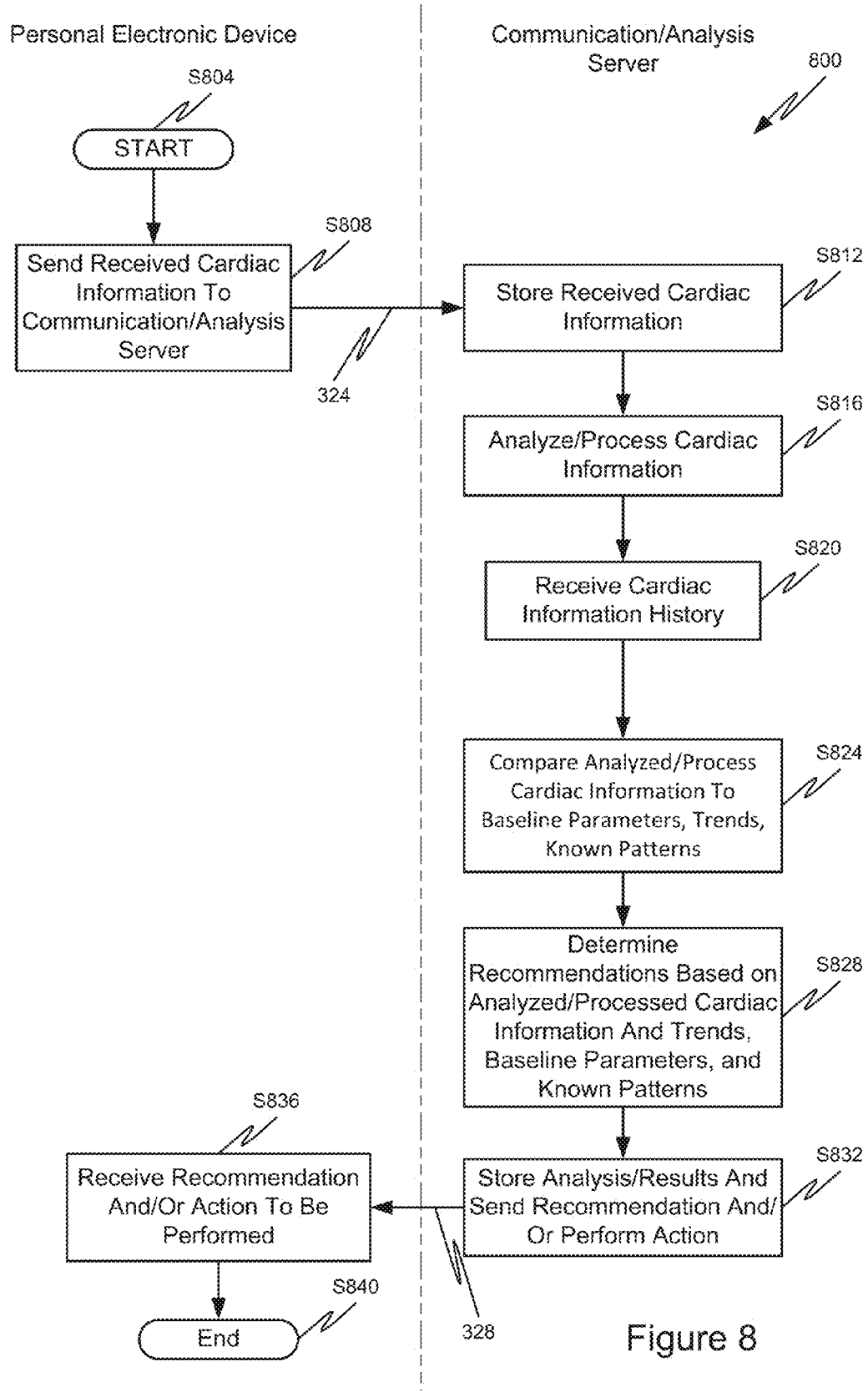
FIG. 8 is a flow diagram depicting a third method associated with a personal electronic device in accordance with an exemplary embodiment of the present disclosure.

Referring now to FIG. 8, a method 800 for processing a detected heart signal 116 of a user 104 will be discussed in accordance with embodiments of the present disclosure. Method 800 is in embodiments, performed by a device, such as a personal electronic device 112 and/or a communication/analysis server 316. More specifically, one or more hardware and software components may be involved in performing method 800. In one embodiment, one or more of the previously described modules and/or devices perform one or more of the steps of method 800. The method 800 may be executed as a set of computer-executable instructions executed by a computer system or personal electronic device and encoded or stored on a computer-readable medium. Hereinafter, the method 800 shall be explained with reference to systems, components, modules, software, etc. described with FIGS. 1-7.

Method 800 may continuously flow in a loop, flow according to a timed event, or flow according to a change in an operating or status parameter. Method 800 is initiated at step S804 where a personal electronic device 112 may initiate the processing of a detected heart signal 116. As previously discussed, the unobtrusively detected heart signal 116 may be stored locally as cardiac information 324 at the personal electronic device 112 or the unobtrusively detected heart signal 116 may be sent or transmitted to the communication/analysis server 316. Therefore, the Method 800 may first retrieve any store cardiac information 324 from the cardiac data recorder 412 and proceed to step S808, where the cardiac information is sent to the communication/analysis server 316 as cardiac information 324. At step S812, the communication/analysis server 316 may receive the cardiac information 324 and store the cardiac information, for information by the cardiac data recorder 448. Method 800 then proceeds to step S816 where the cardiac information is analyzed and processed.

As previously discussed, the cardiac data analyzer 452 may be responsible for carrying out the analysis/processing of the cardiac information to locate, or otherwise determine, possible heart rate and/or heart rhythm anomalies. As another example, at step S816, the analysis and processing may further include determining one or more values associated with a QRS complex of an unobtrusively detected heart rate signal. Such values may include, but are not limited to elapsed time between one or more adjacent QRS complexes, the duration of the QRS complex, and the absence and detectability of P wave. Further, additional cardiac information history may be received at step S820. Such information may be received from the patient information database 320 and/or from the personal electronic device 112. The additional cardiac information may comprise cardiac information history specific to the user 104 (e.g. additional cardiac information for a specified period of time), and or may include baseline parameters, trends and any known patterns indicative of a heart rate or rhythm anomaly. At step S824, the analyzed and processed cardiac information, including any determined values associated with the QRS complex, such as the elapsed time between adjacent QRS complexes, may then be compared to the baseline parameters, trends, and known patterns received in step S820, if any.

Method 800 then proceeds to step S8280 where the analyzed cardiac information and/or the determine recommendations are stored, and further recommendations and/or results based on the analyzed and processed cardiac information, trends, baseline parameters, and known patterns are determined. For instance, the previously determined values associated with the QRS complex may be compared to known parameters that indicate a cardiac anomaly is present. As one example, the QRS complexes may be detected at and may be occurring at irregular intervals; such irregular intervals may indicate atrial fibrillation. Based on the detected cardiac anomaly, a notification may be determined at step S828 that is specific to the detected anomaly. For example, if the detected cardiac information for a user 104 indicates that the ORS is irregular, slow, or rapid, a recommendation to seek medical attention for further testing may be determined. The determined notification may then be sent to the user and/or the determined action may be performed at step S832. For example, in some instances, the communication/analysis server may alert health care provides to the anomaly detected by the cardiac data analyzer 452. In other embodiments, and depending on the anomaly detected, the communication/analysis server 316 may even dial 9-1-1. Method 800 then proceeds to step 836 where the recommendation and/or action is received at the personal electronic device 112. The recommendation may then be provided to the user 112 in a notification and or the determined action may be performed. Method 800 then ends at step S840.

Figure 9:
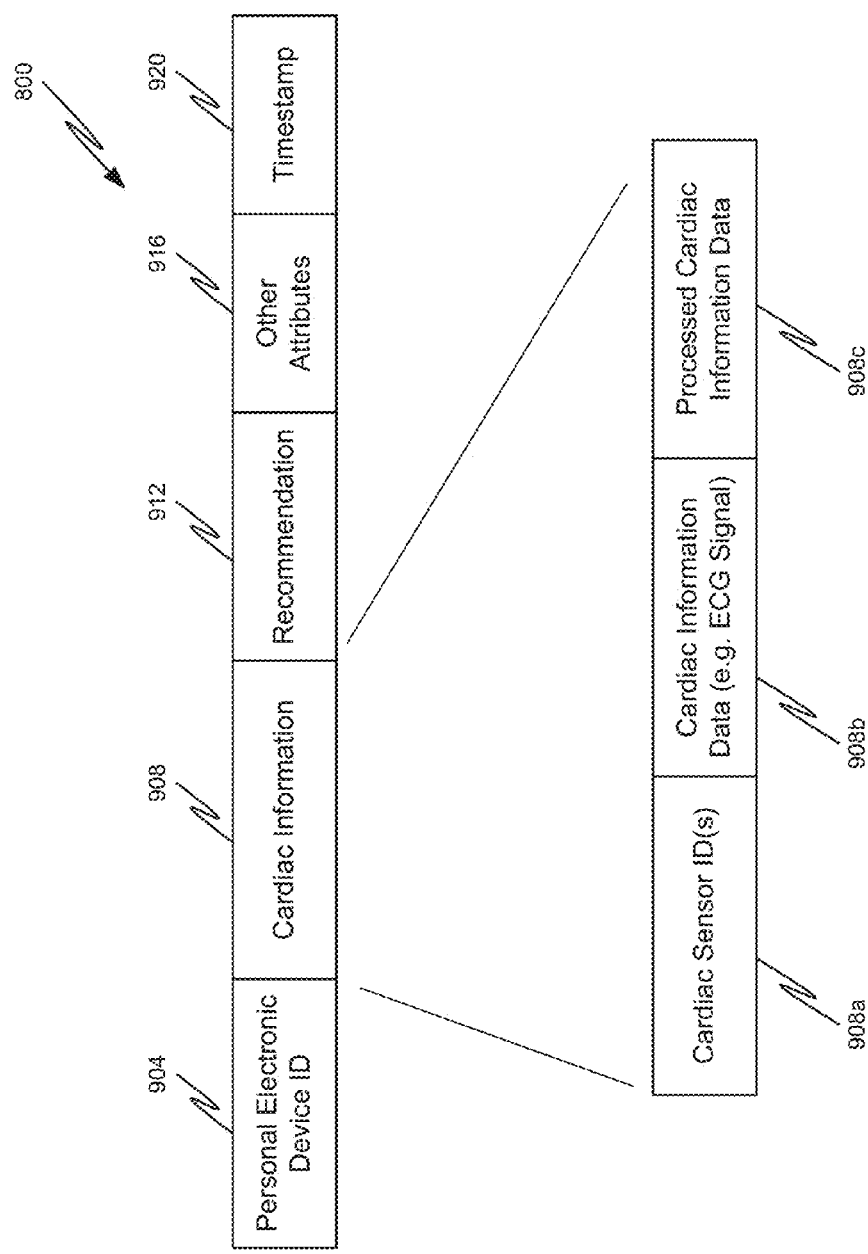
FIG. 9 depicts a data structure in accordance with an exemplary embodiment of the present disclosure.

With reference to FIG. 9, details of a data structure 900 will be described in accordance with embodiments of the present disclosure. In some embodiments, the data structure 900 can be used to further define attributes and/or metadata about information stored in the personal electronic device 112, communication/analysis server 316, and/or transmitted from a personal electronic device 112 and received at a site monitor 312. The data structure 900 may be partially or completely stored in a FIFO buffer, memory 404/444, the patient information database 320, and/or in any other computer memory that is maintaining an instance of information for a user 104. Examples of fields that may be provided in the data structure 900 include, without limitation, a personal electronic device identification field 904, cardiac sensor information field 908, one or more recommendations field 912, other attributes field, and a timestamp field 920.

In some embodiments, the personal electronic device identification field 904 may comprise information that enables a unique identification of the personal electronic 112 within a communication network 308. For instance, a pseudo-randomly generated personal electronic device identification number may be contained in the personal electronic device identification field 904. Other examples of personal electronic device information include, without limitation, a phone number, an IP address, an Electronic Serial Number (ESN), and so on.

The cardiac sensor information field 908 may comprise information relating to a detected heart signal 116 of user 104 and may correspond to cardiac information 324. For example, the cardiac sensor information field 908 may include, without limitation, a cardiac sensor ID(s) field 908A, cardiac information data field (such as a raw EKG signal), and any processed cardiac information data, 908C. Although a cardiac sensor ID(s) field 908A, cardiac information data field, and any processed cardiac information data are illustrated in FIG. 9, it should be noted that the cardiac information may include more or less information fields.

The other attributes information field 916 may comprise information similar to the personal electronic device identification field 904, but the attributes information may not necessarily correspond to information used in connection with the personal electron device 112. For example, the communication/analysis server may be capable of receiving heart rate, heart rhythm and other cardiac information for the same heart from different personal electronic devices. For example, a user may utilize a personal electronic device 112A and a personal electronic device 112D; thus, any heart rate and rhythm information and any other cardiac information associated therewith may be received at the communication/analysis server 316 and tagged as belonging to the same user, or heart, using the other attribute information field 916. Other examples of information that may be maintained in the other attributes information field 912 may include, without limitation, anomaly update information, user id information, identification that may be used to link or identify user 104 to/in an information database, such as a medical database containing all or some of user 104's medical records and a patient information data base 320, and so on.

The timestamp information field 920 may comprise information that specifies a time at which the cardiac information in the cardiac information field was sent and/or received. In the foregoing description, for the purposes of illustration, methods were described in a particular order.

It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor (GPU or CPU) or logic circuits programmed with the instructions to perform the methods (FPGA). These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments were described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While illustrative embodiments of the disclosure have been described in detail herein, it is to be understood that the inventive concepts may be otherwise variously embodied and employed, and that the appended claims are intended to be construed to include such variations, except as limited by the prior art.

What is claimed is:

1. A method comprising:
receiving, by a communication interface of an analysis server, information from a first personal electronic device and a second personal electronic device, the first personal electronic device communicatively coupled to an earbud and including a communication interface configured to wirelessly communicate with the analysis server, the second personal electronic device including a wired handset and a telephone, the information from the first personal electronic device including location information associated with first and second electrodes of the first personal electronic device, wherein the location information associated with the first and second electrodes of the first personal electronic device includes a first location where the first electrode contacts a user's body and a second location where the second electrode contacts the user's body, the information from the first personal electronic device further including a first heart signal that is a differential voltage corresponding to an electrical activity of the user's heart along an axis that corresponds to an electrical pathway between the first and second electrodes, wherein the differential voltage is amplified and measured, by the first personal electronic device and between the first and second electrodes associated with the first personal electronic device, the information from the second personal electronic device including location information associated with third and fourth electrodes of the second personal electronic device, wherein the location information associated with the third and fourth electrodes of the second personal electronic device includes a third location where the third electrode contacts the user's body and a fourth location where the fourth electrode contacts the user's body, the information from the second personal electronic device further including a second heart signal that is a differential voltage corresponding to an electrical activity of the user's heart along an axis that corresponds to an electrical pathway between the third and fourth electrodes, wherein the differential voltage is amplified and measured, by the second personal electronic device and between the third and fourth electrodes associated with the second personal electronic device;

analyzing, automatically by a cardiac analyzer of the analysis server, the first and second heart signals received from the first and second personal electronic devices in accordance with the location information associated with the first and second electrodes of the first personal electronic device and the location information associated with the third and fourth electrodes of the second personal electronic device, wherein the cardiac analyzer performs a first analysis of the first heart signal in accordance with a first angle corresponding to an electrical pathway through the user's heart between the first electrode and the second electrode when the first electrode is in contact with the user's left ear, the cardiac analyzer performs a second analysis of the first heart signal in accordance with a second angle corresponding to an electrical pathway through the user's heart between the first electrode and the second electrode when the first electrode is in contact with the user's right ear, the cardiac analyzer performs a third analysis of the second heart signal in accordance with a first angle corresponding to an electrical pathway through the user's heart between the third electrode and the fourth electrode when the third electrode is in contact with the user's left ear, the cardiac analyzer performs a fourth analysis of the second heart signal in accordance with a second angle corresponding to an electrical pathway through the user's heart between the third electrode and the fourth electrode when the third electrode is in contact with the user's right ear;

determining, automatically by the analysis server, an anomaly based on at least one of the first analysis, the second analysis, the third analysis, or the fourth analysis; and providing, automatically by the analysis server, an indication of the determined anomaly to at least one of the first personal electronic device or the second personal electronic device.

2. The method of claim 1, wherein a first use of the first personal electronic device is at least one of communicating, playing music, displaying video, displaying one or more images, or displaying textual information.

3. The method of claim 2, wherein the second electrode is located on the first personal electronic device at a position such that a limb of the user's body contacts the second electrode during the first use of the first personal electronic device.

4. The method of claim 2, wherein the first electrode is located on the ear bud of the first personal electronic device and the second electrode is located on the first personal electronic device at a position such that a limb of the user's body contacts the second electrode during the first use of the first personal electronic device.

5. The method of claim 1, further comprising:
receiving, by the analysis server, user identification information and personal electronic device identification information.

6. The method of claim 5, further comprising:
retrieving, by the analysis server, cardiac information from a medical database of cardiac information, wherein the retrieved cardiac information is based on the user identification information; and
determining the anomaly by comparing at least one of the first heart signal or the second heart signal to the cardiac information retrieved from the medical database of cardiac information.

7. The method of claim 1, wherein the second electrode is located on the first personal electronic device.

8. A tangible computer-readable medium comprising microprocessor-executable instructions that, when executed by a microprocessor, cause the microprocessor to perform the method according to claim 1.

9. An analysis server communicatively coupled to a first and second personal electronic device, the analysis server comprising:

a communication interface that receives information from the first personal electronic device and the second personal electronic device, the first personal electronic device communicatively coupled to an earbud and including a communication interface configured to wirelessly communicate with the analysis server, the second personal electronic device including a wired handset and a telephone, the information from the first personal electronic device including location information associated with first and second electrodes of the first personal electronic device, wherein the location information associated with the first and second electrodes of the first personal electronic device includes a first location where the first electrode contacts a user's body and a second location where the second electrode contacts the user's body, the information from the first personal electronic device further including a first heart signal that is a differential voltage corresponding to an electrical activity of the user's heart along an axis that corresponds to an electrical pathway between the first and second electrodes, wherein the differential voltage is amplified and measured, by the first personal electronic device and between the first and second electrodes associated with the first personal electronic device, the information from the second personal electronic device including location information associated with third and fourth electrodes of the second personal electronic device, wherein the location information associated with the third and fourth electrodes of the second personal electronic device includes a third location where the third electrode contacts the user's body and a fourth location where the fourth electrode contacts the user's body, the information from the second personal electronic device further including a second heart signal that is a differential voltage corresponding to an electrical activity of the user's heart along an axis that corresponds to an electrical pathway between the third and fourth electrodes, wherein the differential voltage is amplified and measured, by the second personal electronic device and between the third and fourth electrodes associated with the second personal electronic device; and a cardiac analyzer that analyzes the first and second heart signals received from the first and second personal electronic devices in accordance with the location information associated with the first and second electrodes of the first personal electronic device and the location information associated with the third and fourth electrodes of the second personal electronic device, wherein the cardiac analyzer performs a first analysis of the first heart signal in accordance with a first angle corresponding to an electrical pathway through the user's heart between the first electrode and the second electrode, the cardiac analyzer performs a second analysis of the second heart signal in accordance with a first angle corresponding to an electrical pathway through the user's heart between the third electrode and the fourth electrode, and the cardiac analyzer determines an anomaly based on the first analysis or the second analysis, wherein the analysis server provides an indication of the determined anomaly to at least one of the first personal electronic device or the second personal electronic device.

10. The analysis server of claim 9, wherein a first use of the first personal electronic device is at least one of communicating, playing music, displaying video, displaying one or more images, or displaying textual information.

11. The analysis server of claim 10, wherein the second electrode is located on the first personal electronic device at a position such that a limb of the user's body contacts the second electrode during the first use of the first personal electronic device.

12. The analysis server of claim 10, wherein the first electrode is located on the ear bud of the first personal electronic device and the second electrode is located on the first personal electronic device at a position such that a limb of the user's body contacts the second electrode during the first use of the first personal electronic device.

13. The analysis server of claim 9, further comprising:
receiving, by the analysis server, user identification information and personal electronic device identification information.

14. The analysis server of claim 13, wherein the analysis server retrieves cardiac information based on the user identification information from medical database of cardiac information; and the analysis server determines the anomaly by comparing at least one of the first heart signal or the second heart signal to the cardiac information retrieved from the medical database of cardiac information.

15. The analysis server of claim 9, wherein the second electrode is located on the first personal electronic device.

16. An analysis server communicatively coupled to a first and second personal electronic device, the analysis server comprising:
a communication interface that receives information from the first personal electronic device and the second personal electronic device, the first personal electronic device communicatively coupled to an earbud and including a communication interface configured to wirelessly communicate with the analysis server, the second personal electronic device including a wired handset and a telephone, the information from the first personal electronic device including location information associated with first and second electrodes of the first personal electronic device, wherein the location information associated with the first and second electrodes of the first personal electronic device includes a first location where the first electrode contacts a user's body and a second location where the second electrode contacts the user's body, the information from the first personal electronic device further including a first heart signal that is a differential voltage corresponding to an electrical activity of the user's heart along an axis that corresponds to an electrical pathway between the first and second electrodes, wherein the differential voltage is amplified and measured, by the first personal electronic device and between the first and second electrodes associated with the first personal electronic device, the information from the second personal electronic device including location information associated with third and fourth electrodes of the second personal electronic device, wherein the location information associated with the third and fourth electrodes of the second personal electronic device includes a third location where the third electrode contacts the user's body and a fourth location where the fourth electrode contacts the user's body, the information from the second personal electronic device further including a second heart signal that is a differential voltage corresponding to an electrical activity of the user's heart along an axis that corresponds to an electrical pathway between the third and fourth electrodes, wherein the differential voltage is amplified and measured, by the second personal electronic device and between the third and fourth electrodes associated with the second personal electronic device; and a cardiac analyzer that analyzes the first and second heart signals received from the first and second personal electronic devices in accordance with the location information associated with the first and second electrodes of the first personal electronic device and the location information associated with the third and fourth electrodes of the second personal electronic device, wherein the cardiac analyzer performs a first analysis of the first heart signal in accordance with a first angle corresponding to an electrical pathway through the user's heart between the first electrode and the second electrode when the first electrode is in contact with the user's left ear, the cardiac analyzer performs a second analysis of the first heart signal in accordance with a second angle corresponding to an electrical pathway through the user's heart between the first electrode and the second electrode when the first electrode is in contact with the user's right ear, the cardiac analyzer performs a third analysis of the second heart signal in accordance with a first angle corresponding to an electrical pathway through the user's heart between the third electrode and the fourth electrode when the third electrode is in contact with the user's left ear, the cardiac analyzer performs a fourth analysis of the second heart signal in accordance with a second angle corresponding to an electrical pathway through the user's heart between the third electrode and the fourth electrode when the third electrode is in contact with the user's right ear, and the cardiac analyzer determines an anomaly based on at least one of the first analysis, the second analysis, the third analysis, or the fourth analysis, wherein the analysis server provides an indication of the determined anomaly to at least one of the first personal electronic device or the second personal electronic device.

17. The analysis server of claim 16, wherein a first use of the first personal electronic device is at least one of communicating, playing music, displaying video, displaying one or more images, or displaying textual information.

18. The analysis server of claim 17, wherein the second electrode is located on the first personal electronic device at a position such that a limb of the user's body contacts the second electrode during the first use of the first personal electronic device.

19. The analysis server of claim 17, wherein the first electrode is located on the ear bud of the first personal electronic device and the second electrode is located on the first personal electronic device at a position such that a limb of the user's body contacts the second electrode during the first use of the first personal electronic device.

20. The analysis server of claim 16, further comprising:
receiving, by the analysis server, user identification information and personal electronic device identification information.

21. The analysis server of claim 20, wherein the analysis server retrieves cardiac information based on the user identification information from a medical database of cardiac information; and the analysis server determines the anomaly by comparing at least one of the first heart signal or the second heart signal to the cardiac information retrieved from the medical database of cardiac information.

* * * * *